United States Patent
Brown

(10) Patent No.: US 11,826,304 B2
(45) Date of Patent: Nov. 28, 2023

(54) STEAMING STATION

(71) Applicant: Sheila Denise Brown, Bowie, MD (US)

(72) Inventor: Sheila Denise Brown, Bowie, MD (US)

(*) Notice: Subject to any disclaimer, the term of this patent is extended or adjusted under 35 U.S.C. 154(b) by 0 days.

(21) Appl. No.: 17/848,537

(22) Filed: Jun. 24, 2022

(65) Prior Publication Data

US 2023/0172803 A1 Jun. 8, 2023

Related U.S. Application Data

(60) Provisional application No. 63/285,198, filed on Dec. 2, 2021.

(51) Int. Cl.
*A61H 33/12* (2006.01)

(52) U.S. Cl.
CPC .................................. *A61H 33/12* (2013.01)

(58) Field of Classification Search
CPC ....................................................... A61H 33/12
USPC ............................................................. 4/524
See application file for complete search history.

(56) References Cited

U.S. PATENT DOCUMENTS

| | | | | |
|---|---|---|---|---|
| 3,707,971 | A | * | 1/1973 | Yamamoto ............. A61H 33/12 4/537 |
| 3,949,743 | A | * | 4/1976 | Shanbrom ......... A61M 15/0003 128/200.14 |
| 4,816,644 | A | * | 3/1989 | Frank ..................... A61H 33/12 4/537 |
| 6,904,624 | B2 | | 6/2005 | Leung et al. |
| 8,011,731 | B2 | | 9/2011 | Goddu |
| D656,356 | S | * | 3/2012 | Cheng ............................ D6/601 |
| 8,468,628 | B1 | | 6/2013 | Cheng |
| 8,850,642 | B2 | | 10/2014 | Rasmussen |
| D894,371 | S | | 8/2020 | Farone et al. |
| 10,729,871 | B2 | | 8/2020 | Niedermann et al. |
| 2014/0100490 | A1 | | 4/2014 | Chelgren |
| 2020/0281791 | A1 | | 9/2020 | Miller |

* cited by examiner

*Primary Examiner* — Huyen D Le
(74) *Attorney, Agent, or Firm* — Howard University School of Law; Darrell G. Mottley

(57) ABSTRACT

A steaming station may include a hinged lid that allows the user to place a concave bowl with hot liquids within the inside cavity. Once the steaming station is closed with hot liquids and medicinal herbs, the user can then kneel or sit with the steaming station in front of them and place their face onto the rounded cavity of the lid to receive the benefits of the steam for extended periods of time.

20 Claims, 3 Drawing Sheets

STEAMING STATION

CROSS-REFERENCE TO RELATED APPLICATIONS

This application claims priority to U.S. Application No. 63/285,198 filed Dec. 2, 2021, the contents therein is incorporated by references in its entirety.

FIELD

The field of disclosure generally relates to steaming station that uses hot liquids and steam/vapor to help the user mitigate breathing complications such as asthma, congestion, and other similar conditions.

BACKGROUND

Steam has been known to help soothe and treat acute and chronic breathing conditions, including nasal congestion, sore throat, allergies, asthma, and many others.

SUMMARY

The following summary presents some concepts in the disclosure in a simplified manner as a prelude to the more detailed description provided below. Aspects of the present disclosure relate to an ergonomic steaming station.

In one aspect, the steaming station may include an enclosed inside cavity capable of holding a concave bowl filled with hot liquid.

In one aspect, the steaming station may include a hinged lid with a circular opening for the user to place their face on.

In one aspect, the steaming station may include two wedges on the underside of the steaming station, which place the steaming station at an angle between 25 and 32 degrees from a support surface.

In one aspect, the steaming station may include a terry cloth pillow that is to be placed on top of the lid of the steaming station.

In one aspect, the steaming station may include a set of handles on two opposing sides of the steaming station for easy transport.

In one aspect, the steaming station may include the use of herbs and oils or medicinal extracts to be placed on the bowl that holds the liquids.

In one aspect, the steaming station may include an incline angle at 28 degrees from a support surface.

In another aspect, the steaming station may include incline angle at 28.072 degrees from a support surface.

In another aspect, the steaming station may include a water-resistance resin on the interior surfaces and exterior surfaces.

In another aspect, an ergonomic steaming station may include a bowl with hot liquid and optional medicinal herbs placed in a box-shaped container with a hinged lid, so as to emit a vapor or steam from an enclosed space to an opening to help the user mitigate breathing complications such as asthma, congestion, and other similar conditions.

BRIEF DESCRIPTION OF THE DRAWINGS

The foregoing summary as well as the following detailed description, considered in conjunction with the accompanying drawings, provides a better understanding of the disclosure, in which like reference numbers refer to like element.

DETAILED DESCRIPTION

Figure 1:
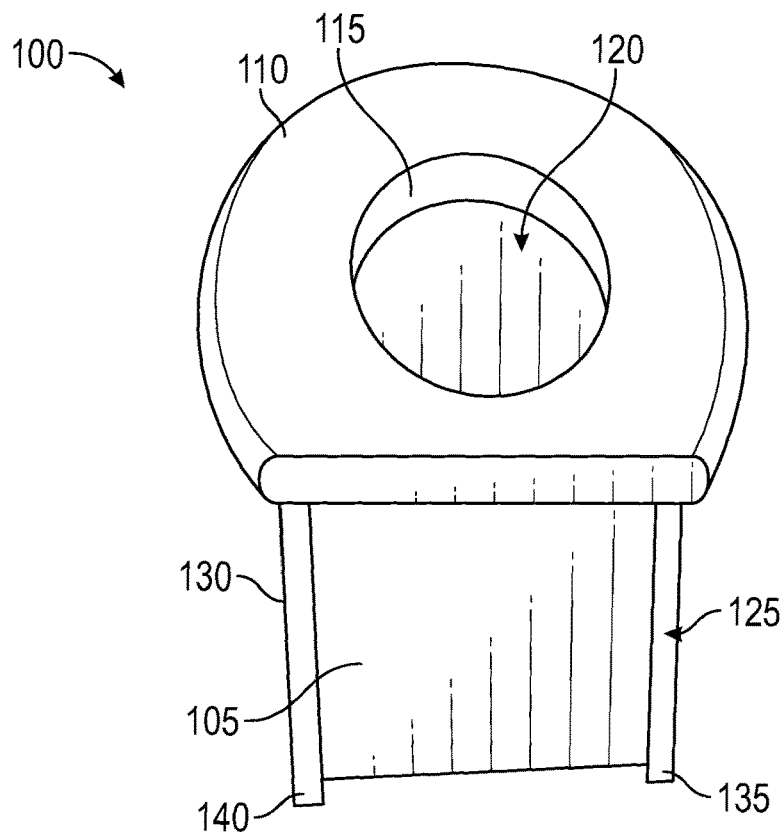
FIG. 1 depicts a front side view of the steaming station and depicted in the figure is the lid with the round opening for the user's face. Also depicted is the front wall of the inside cavity.

As illustrated in FIGS. 1-5, a steaming/vapor station 100 allows the placement of a concave bowl 500 filled with a hot liquid and herbs 505 within an inside cavity 120. An infused-herb steam or vapor emerges from the bowl flows up the inside cavity 120 through a lid cavity 115 of a rounded lid 110 so the user can inhale the steam or vapor in an ergonomical position provided by the ergonomic wedges 135, 145, 200.

Referring to FIG. 1, the steaming station 100 includes an inside cavity 120 in the form of a box 105, 125, 130. The steaming station 100 contains a round lid 110, with a facial cavity 115 for a user to place their face on top of the lid. In one construction, the facial cavity 115 has a circular opening. In the other constructions, the facial cavity 115 could be other shapes such as an oval. The front of the lid 100 includes a straight edge surface configured to engage or abut the upper torso of a user. The steaming station 100 includes left and right ergonomic wedges 140, 135 that place the steaming station at an ergonomical angle, measured from a horizontal plane (planar support surface), between 28 and 32 degrees for the user's comfort to reduce spline strain while using the station. The steaming station 100 round lid 110 may also contain two small hooks at opposite ends of the round lid 110 to secure the face pillow 400.

Figure 2:
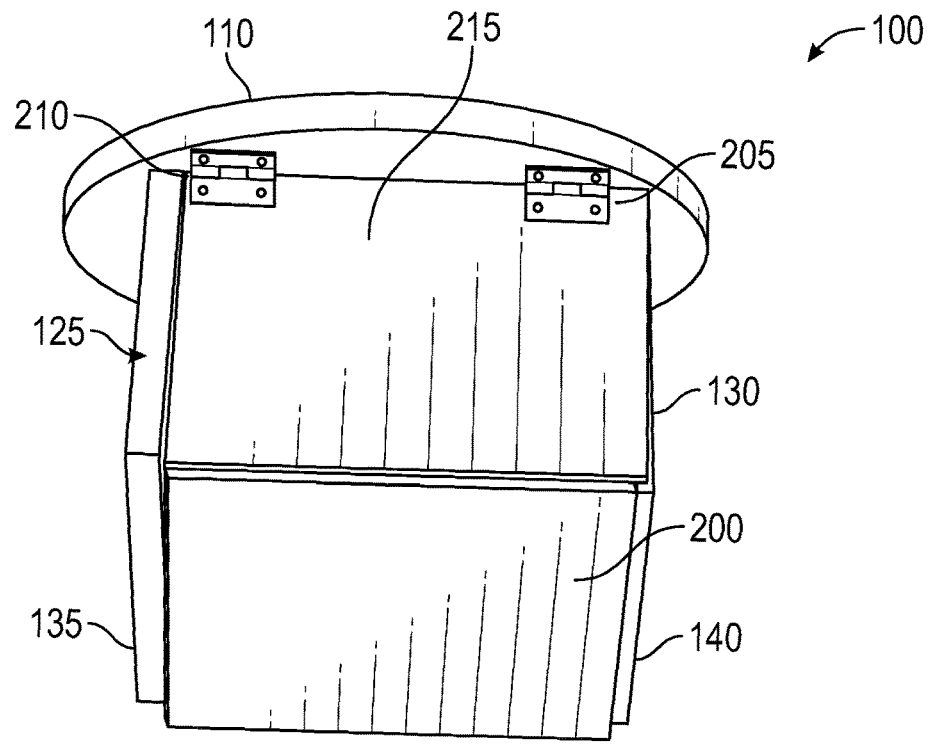
FIG. 2 depicts a rear perspective view of the steaming station. Depicted in the figure are the back wall of the inside cavity as well as the back portion of the lid, both of which are connected through two metal hinges. Also depicted are the right and left walls of the inside cavity and the back side of the ergonomic wedges.

Referring to FIG. 2, the steaming station 100 includes a back wall 215 that encloses the box inside cavity 120, as well as the right-side wall 125, and the left side wall 130. The rounded lid 110 of the steaming station 100 is connected by a left hinge 205 and a right hinge 210 to the inside cavity 120, which allows for opening and closing of said rounded lid 110. The steaming station 100 also includes a back ergonomic wedge 200 connected to the left ergonomic wedge 140 and the right ergonomic wedge 210.

Figure 3:
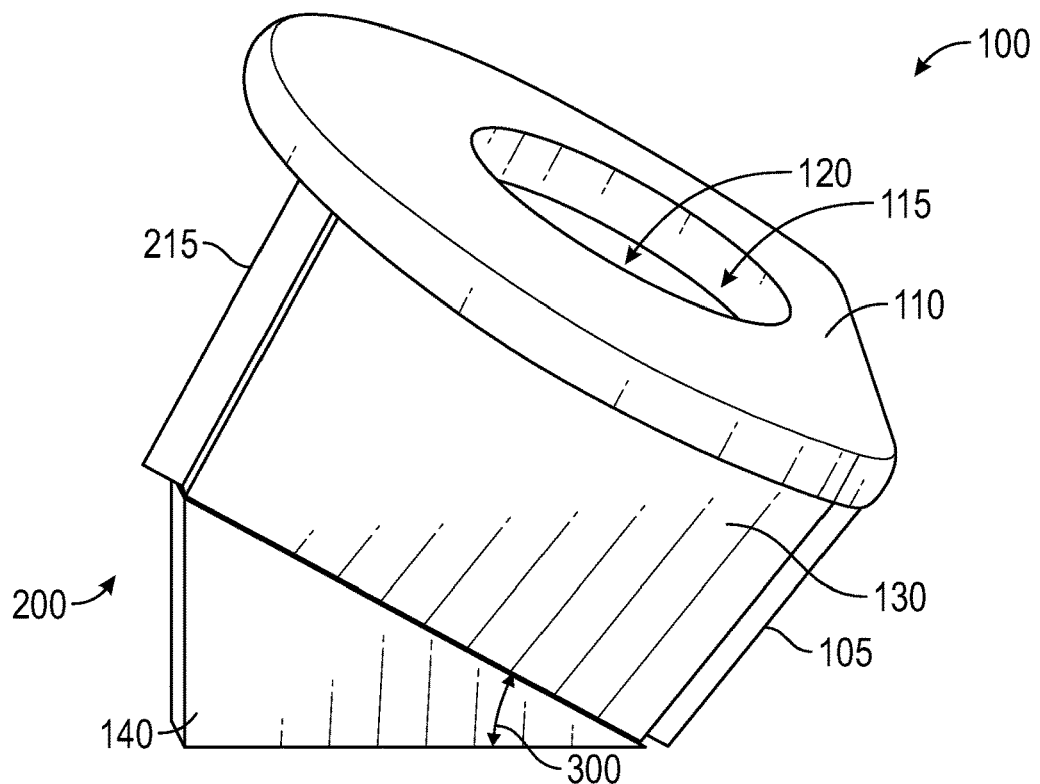
FIG. 3 depicts the left side view of the steaming station. Depicted in this figure are the left side of the lid, the left wall of the steaming station, and the left wall of the ergonomic wedge.

Referring to FIG. 3, the steaming station 100 includes the left ergonomic wedge that place the steaming station 100 at an ergonomic angle 300 of at least 28 degrees and at most 32 degrees. The right ergonomic wedge 135 (not depicted in FIG. 3) also includes the ergonomic angle 300 of at least 28 degrees and at most 32 degrees. In one construction, the angle 300 may be set at 28.072 degrees. This angle enables the user to comfortably rest their head on the lid 110 while using the device without putting additional strain on their neck, spine or back.

Figure 4:
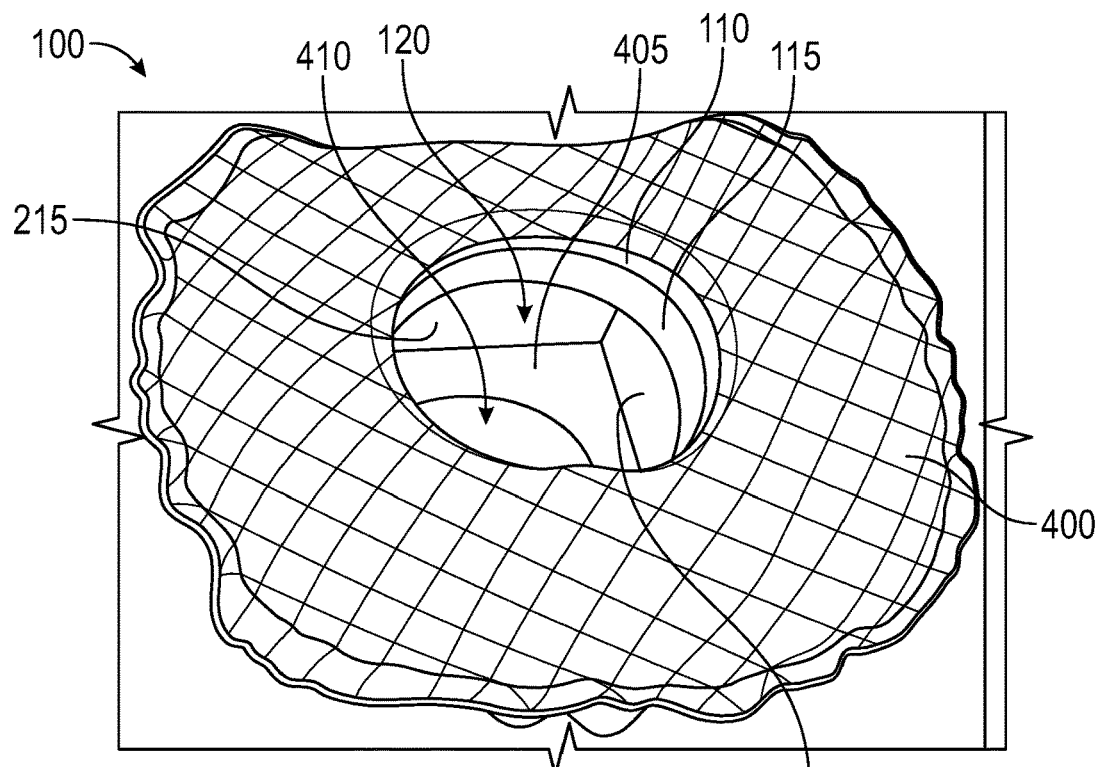
FIG. 4 depicts the steaming station from a front and downward angle view. Depicted in the figure is the lid in a closed position with its facial opening. Also depicted is a terry cloth pillow placed on top of the lid, which also has a facial opening matching the size of the opening of the lid. Also depicted in this figure is the inside of the inside cavity through the opening in the facial pillow and the lid.

Referring to FIG. 4, the steaming station 100 may include a removable facial pillow 400 provided on top of the round lid 110 depicted in the closed position. The pillow could be made in various constructions for use with the steaming station and provide comfort to the user. In one construction, the facial pillow 400 may have terry cloth covering with an interior made a soft foam material. The facial pillow 400 may also contain two elastic loops at two opposing ends of the facial pillow 400 that go over the two hooks in the round lid 110 so the pillow remains fastened on the round lid 110. The steaming station 100 may also include a station floor 405 that enclose the inside cavity 120. The steaming station 100 may also include a heat resistant mantle 410 placed on top of the steaming station floor 405. In one construction, the heat resistant mantle is made out of cork material.

Figure 5:
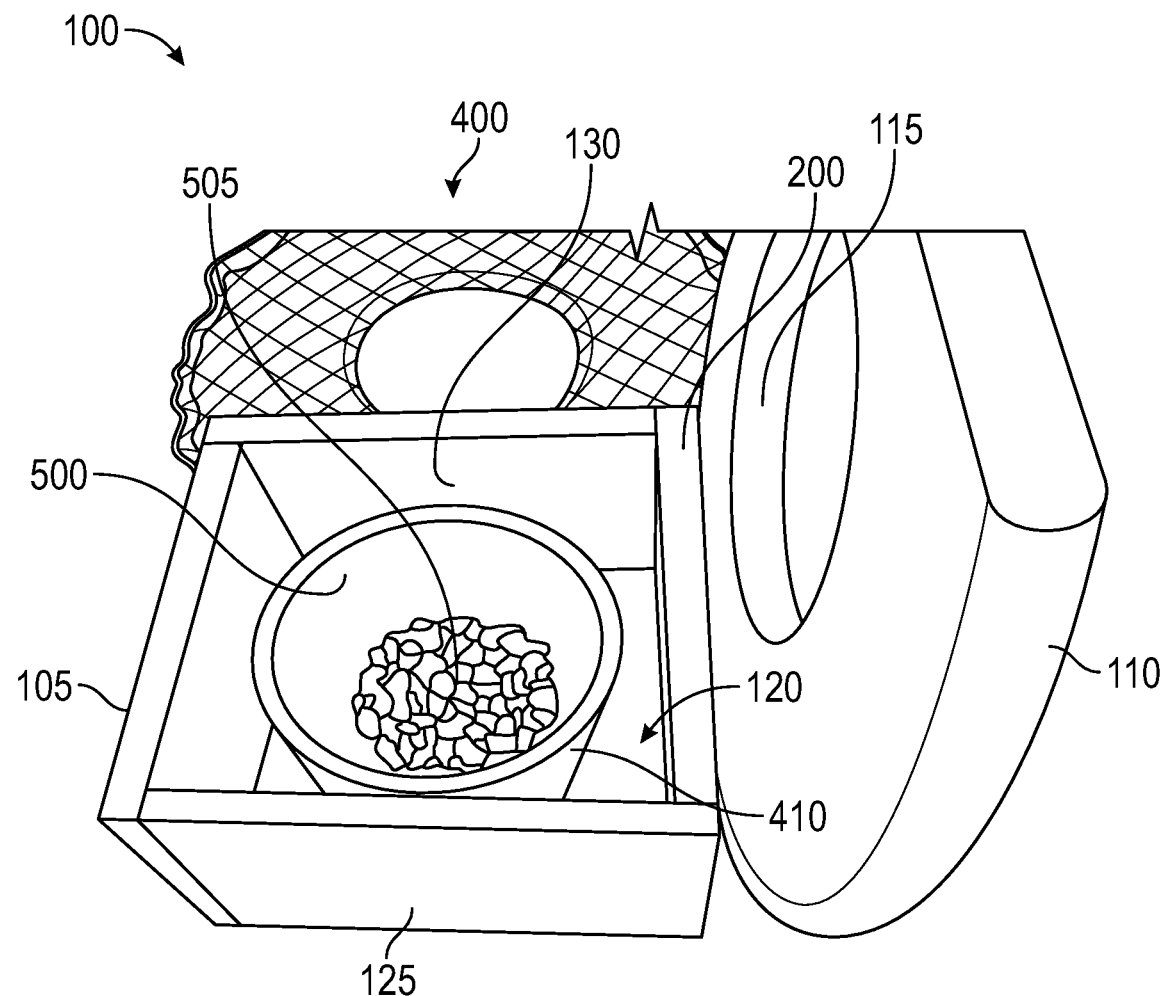
FIG. 5 depicts the right front side view of the steaming station from a downward angle. Depicted in the figure is the hinged lid in an open position with the facial pillow placed on the floor. Depicted in the figure are the inside cavity containing a concave bowl filled with liquid and medicinal herbs.

Referring to FIG. 5, the steaming station 100, depicted in an open configuration, includes a concave bowl 500 containing herbs and hot liquid 505, which produce the steam.

In some constructions, the steaming station 100 which includes back wall 215 that encloses the box inside cavity 120, as well as the right-side wall 125, and the left side wall 130; left and right ergonomic wedges 140, 135 can be made of a wood material, a wood panel or a plastic material. In other constructions, the station 100 could be made of a plastic material and molded into the various shapes. In one construction, the left and right ergonomic wedges 140, 135 may be integrated with the right-side wall 125, and the left side wall 130, respectively, to form unitary components for the right side and left side. In another construction, ergonomic wedges 135, 145, 200 may form a unitary component or platform in which the box form 105, 125, 130 provided thereon. In another construction, the inside cavity 120 surfaces in the box interior and bottom surface of the lid 110 may be sealed with a water-resistant resin to ensure that the steam reliably exits the station through the facial cavity 115. In another construction, the box exterior surface may be sealed with a water-resistant resin. One type of water-resistant resin may be a phenol resin used on plywood or a phenol film for an overlay on plywood. In one construction, the steaming station 100 may include a set of handles on two opposing sides of the steaming station for easy transport.

Aspects of the technology of the present disclosure provides for an ergonomically designed steaming station 100 providing a user with the benefits of steam produced by hot liquids placed inside the steaming station 100, such hot liquids may be mixed with medicines or herbs. The steaming station 100 may include a hinged lid 110 that allows the user to place a concave bowl with hot liquids within the inside cavity. In operation, once the steaming station is closed with hot liquids and medicinal herbs, the user can then kneel or sit with the steaming station 100 in front of them and place their face onto the rounded cavity of the lid to receive the benefits of the steam for extended periods of time.

While the system and methods have been described with reference to exemplary embodiments and constructions, it will be understood by those of ordinary skill in the art that various changes may be made and equivalents may be substituted for elements thereof without departing from the scope of the disclosure.

What is claimed is:

1. A steaming station for a human body, comprising:
   a) an enclosed box having a top end and a bottom end;
   b) a wedge component located at the bottom end of the box, wherein the wedge component includes an incline angle of the box at least 25 to 32 degrees above a support surface; and
   c) a rounded lid having a lid cavity; the lid configured to support a head of a human body with a face of the human body placed within the lid cavity; the lid being hingedly mounted to the top end of the box.

2. The steaming station according to claim 1, further comprising a removably mounted facial pillow disposed on top of the lid.

3. The steaming station according to claim 2, further comprising a cork sheet material on a floor of an inside cavity of the enclosed box and allows for the placement of a round deep dish or bowl thereon.

4. The steaming station of claim 3, wherein the round deep dish or bowl holds hot or steaming liquids.

5. The steaming station according to claim 3, wherein the incline angle is 28.0 degrees.

6. The steaming station according to claim 3, wherein the incline angle is 28.072 degrees.

7. The steaming station according to claim 3, wherein the facial pillow further comprises a terry cloth covering.

8. The steaming station according to claim 3, wherein an interior surface of the box includes a water-resistance resin.

9. The steaming station according to claim 8, wherein an exterior surface of the box includes a water-resistance resin.

10. The steaming station according to claim 8, wherein the incline angle is 28.072 degrees.

11. The steaming station according to claim 10, wherein the wedge component further comprises two wedges.

12. The steaming station according to claim 10, wherein the lid includes a front straight-edge surface.

13. A steaming station for a human body, comprising:
    d) a box having a top end and a bottom end;
    e) a wedge disposed at the bottom end of the box, wherein the wedge includes an incline angle of the box at least 25 to 32 degrees above a planar support surface; and
    f) a rounded lid having a lid cavity; the lid configured to support a head of a human body with a face of the human body placed within the lid cavity; the lid being hingedly mounted to the top end of the box.

14. The steaming station according to claim 13, further comprising a removably mounted facial pillow disposed on top of the lid.

15. The steaming station according to claim 14, further comprising a cork sheet material on a floor of an inside cavity of the box and allows for the placement of a round deep dish or bowl thereon.

16. The steaming station of claim 14, wherein the round deep dish or bowl holds hot or steaming liquids.

17. The steaming station according to claim 14, wherein the incline angle is 28.0 degrees.

18. The steaming station according to claim 14, wherein the incline angle is 28.072 degrees.

19. The steaming station according to claim 14, wherein the facial pillow further comprises a terry cloth covering.

20. The steaming station according to claim 14, wherein an interior surface of the box includes a water-resistance resin thereon.

* * * * *